US009129055B2

(12) United States Patent
Mordaunt et al.

(10) Patent No.: US 9,129,055 B2
(45) Date of Patent: *Sep. 8, 2015

(54) ANATOMICAL RECOGNITION, ORIENTATION AND DISPLAY OF AN UPPER TORSO TO ASSIST BREAST SURGERY

(71) Applicant: Allergan, Inc., Irvine, CA (US)

(72) Inventors: David H. Mordaunt, Los Gatos, CA (US); G. Patrick Maxwell, Nashville, TN (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,800

(22) Filed: Dec. 20, 2013

(65) Prior Publication Data

US 2014/0104272 A1   Apr. 17, 2014

Related U.S. Application Data

(63) Continuation of application No. 13/644,744, filed on Oct. 4, 2012, now Pat. No. 8,648,853, which is a continuation of application No. 12/319,639, filed on Jan. 9, 2009, now Pat. No. 8,294,708.

(60) Provisional application No. 61/010,591, filed on Jan. 9, 2008.

(51) Int. Cl.
*G06T 17/00* (2006.01)
*G06T 15/00* (2011.01)
(Continued)

(52) U.S. Cl.
CPC .............. *G06F 19/3437* (2013.01); *A61F 2/12* (2013.01); *G06F 17/5009* (2013.01); *G06K 9/00201* (2013.01); *G06T 7/608* (2013.01); *G06T 15/08* (2013.01); *G06T 19/20* (2013.01); *G06K 2209/05* (2013.01); *G06T 2200/04* (2013.01); *G06T 2207/10028* (2013.01); *G06T 2207/20044* (2013.01); *G06T 2207/30068* (2013.01);
(Continued)

(58) Field of Classification Search
CPC combination set(s) only.
See application file for complete search history.

(56) References Cited

U.S. PATENT DOCUMENTS

| 4,856,074 A | 8/1989 | Nagaoka |
| 5,513,276 A | 4/1996 | Theodoracatos |

(Continued)

OTHER PUBLICATIONS

Oren M. Tepper, MD, Kevin Small, BA, Lauren Rudolph, BA, Mihye Choi, MD, Nolan Karp, MD, Virtual 3-dimensional modeling as a valuable adjunct to aesthetic and reconstructive breast surgery, Oct. 2006, The American Journal of Surgery, vol. 192, Issue 4, pp. 548-551.*

(Continued)

*Primary Examiner* — Leon T Cain, II
(74) *Attorney, Agent, or Firm* — Linda Allyson Nassif

(57) ABSTRACT

Various methods, techniques or modules are provided to allow for the automated analysis of the 3-D representation of the upper front torso (i) to recognize 3-D anatomical features, (ii) to orient the subject with reference to their anatomy or a display, (iii) to determine dimensional analysis including direct point-to-point lines, 3-D surface lines, and volume values, (iv) to simulate the outcome with the addition of breast implants including breast and nipple positioning, (v) to assist in the selection of the breast implants, and/or (vi) to assist in the planning of breast surgery. The automated analysis is based on the analysis of changes in a 3-D contour map of the upper torso, orientation analysis of 3-D features and planes, color analysis of 3-D features, and/or dimensional analysis of 3-D features and positions of the upper torso.

15 Claims, 17 Drawing Sheets

(51) Int. Cl.

| | | |
|---|---|---|
| G06F 19/00 | (2011.01) | |
| G06K 9/00 | (2006.01) | |
| G06T 7/60 | (2006.01) | |
| G06T 19/20 | (2011.01) | |
| G06T 15/08 | (2011.01) | |
| A61F 2/12 | (2006.01) | |
| G06F 17/50 | (2006.01) | |

(52) U.S. Cl.
CPC ........ *G06T2219/2016* (2013.01); *Y10S 128/92* (2013.01); *Y10S 128/922* (2013.01); *Y10S 128/923* (2013.01)

(56) References Cited

U.S. PATENT DOCUMENTS

| | | |
|---|---|---|
| 6,320,976 B1 | 11/2001 | Murthy |
| 6,564,086 B2 | 5/2003 | Marchitto |
| 6,608,628 B1 | 8/2003 | Ross |
| 6,761,697 B2 | 7/2004 | rubinstenn |
| 6,879,712 B2 | 4/2005 | Tuncay |
| 6,968,075 B1 | 11/2005 | Chang |
| 7,058,439 B2 * | 6/2006 | Eaton et al. .......... 600/425 |
| 7,292,716 B2 | 11/2007 | Kim |
| 7,424,139 B1 | 9/2008 | Stefan |
| 7,519,212 B2 | 4/2009 | Brady |
| 7,555,151 B2 | 6/2009 | Comaniciu |
| 7,587,075 B1 | 9/2009 | Stefan |
| 7,599,537 B1 * | 10/2009 | Stefan et al. .......... 382/128 |
| 7,796,787 B2 | 9/2010 | Wang |
| 8,135,452 B2 | 3/2012 | Dougherty et al. |
| 2002/0035458 A1 | 3/2002 | Kim |
| 2002/0064302 A1 | 5/2002 | Massengill |
| 2002/0092534 A1 | 7/2002 | Shamoun |
| 2003/0013944 A1 | 1/2003 | Benja-athon |
| 2003/0195623 A1 | 10/2003 | Marchitto et al. |
| 2004/0015070 A1 | 1/2004 | Liang |
| 2004/0146191 A1 | 7/2004 | Lu |
| 2005/0264557 A1 | 12/2005 | Kise |
| 2006/0259179 A1 | 11/2006 | Petterson |
| 2007/0081712 A1 | 4/2007 | Huang |
| 2007/0106182 A1 | 5/2007 | Arnett |
| 2007/0219450 A1 | 9/2007 | Azar |
| 2007/0255589 A1 | 11/2007 | Rodriguez |
| 2007/0258656 A1 | 11/2007 | Aarabi |
| 2007/0269111 A1 | 11/2007 | Bolin |
| 2008/0159608 A1 | 7/2008 | Suetens |
| 2008/0260219 A1 | 10/2008 | Witte |
| 2008/0267443 A1 | 10/2008 | Aarabi |
| 2008/0267471 A1 | 10/2008 | Yu et al. |
| 2009/0112130 A1 | 4/2009 | Bengtson |
| 2009/0137908 A1 | 5/2009 | Patwardhan |
| 2009/0174707 A1 | 7/2009 | Mordaunt |
| 2009/0175516 A1 | 7/2009 | Mordaunt |
| 2009/0175517 A1 | 7/2009 | Mordaunt |
| 2009/0196475 A1 | 8/2009 | Demirli |
| 2009/0219289 A1 | 9/2009 | Kalvin |
| 2009/0227904 A1 | 9/2009 | Mordaunt |
| 2010/0142755 A1 | 6/2010 | Brandewie |
| 2010/0189342 A1 | 7/2010 | Parr |
| 2010/0280375 A1 | 11/2010 | Zhang et al. |

OTHER PUBLICATIONS

Cantanuto et al., "Experimental Methodology for Digital breast Shape Analysis and Objective Surgical Outcome Evaluation", Journal of Plastic, Reconstructive and Aesthetic Surgery, XP022472032, vol. 61, No. 3, pp. 314-318 (2008).

Chen, D et al., "Computational Tools for Quantitative Breast Morphometry Based on 3D Scans", Annals of Biomedical Engineering, XP019786092, vol. 38, No. 5, pp. 1703-1718 (2010).

Eder et al., "Three-dimensional Evaluation of Breast Contour and Volume Changes Following Subpectoral Augmentation Mammaplasty over 6 Months", Journal of Plastic, Reconstructive and Aesthetic Surgery, XP028267564, pp. 1152-1160 (2011).

Farinella, GM et al., "Unambiguous Analysis of Woman Breast Shape for Plastic Surgery Outcome Evaluation", Eurographics Italian Chapter Conference, XP55039304, pp. 255-261 (2006).

Farinella, GM et al., "Objective Evaluation of Breast Surgery", Medical Image Computing and Computer Assisted Intervention—MICCAI 2006 4190, pp. 776-783 (2006).

Lee et al., "Measurement Protocol of Women's Nude Breasts Using a 3D Scanning Technique", Applied Ergonomics, 35 (2004), pp. 353-359.

Losken et al., "Validating Three Dimensional Imaging of the Breast", Annals of Plastic Surgery, 2005, 5(5):471-476.

Oren et al., "Virtual 3-Dimensional Modeling as a Valuable Adjunct to Aesthetic and Reconstructive Breast Suregery", The American Journal of Surgery, 192(4): 548-551, 2006.

Qiao et al., "Breast Volume Measurement in Young Chinese Women and Clinical Applications", Aest. Plast. Surg. 21:362-368, 1997.

Tebbetts, "A System for Breast Implant Selection Based on Patient Tissue Characteristics and Implant-Soft Tissue Dynamics", Plast. Reconstr. Surg. 2002, 109(4)1410-1415.

Galdino et al., "Clinical Applications of Three-Dimensional Photography in Breast Surgery", Plast. Reconstr. Surg. 2002, 110(1):58-70.

* cited by examiner

FIG. 7
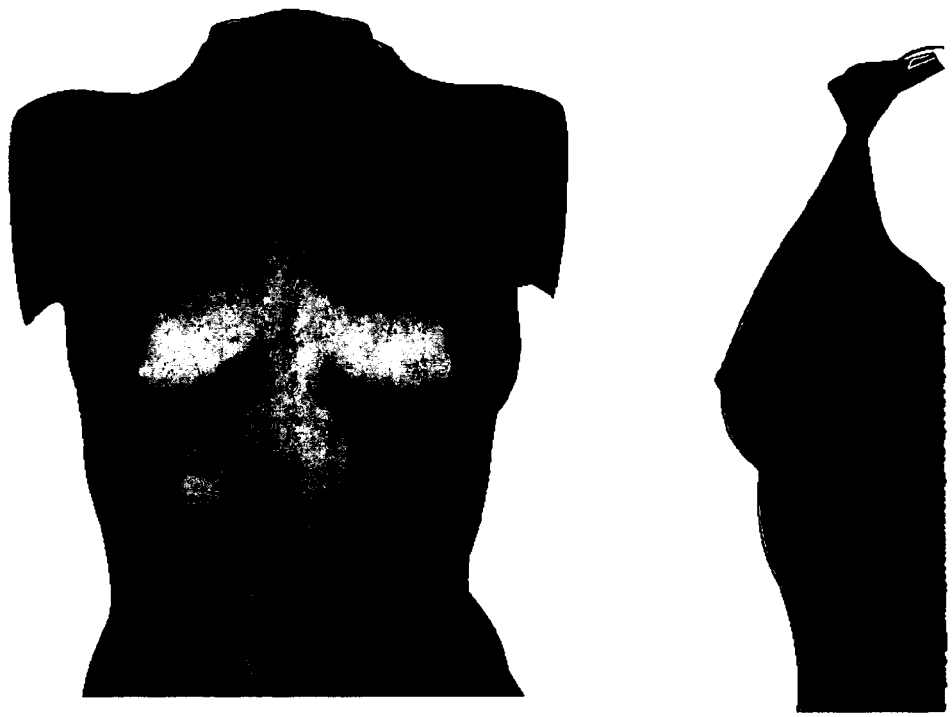
710  720
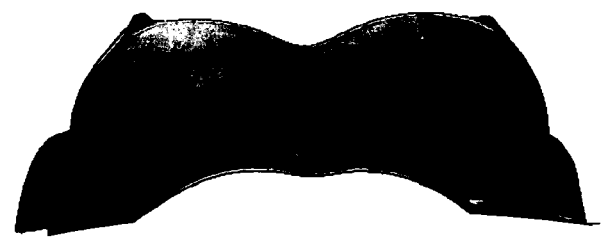
730

FIG. 8
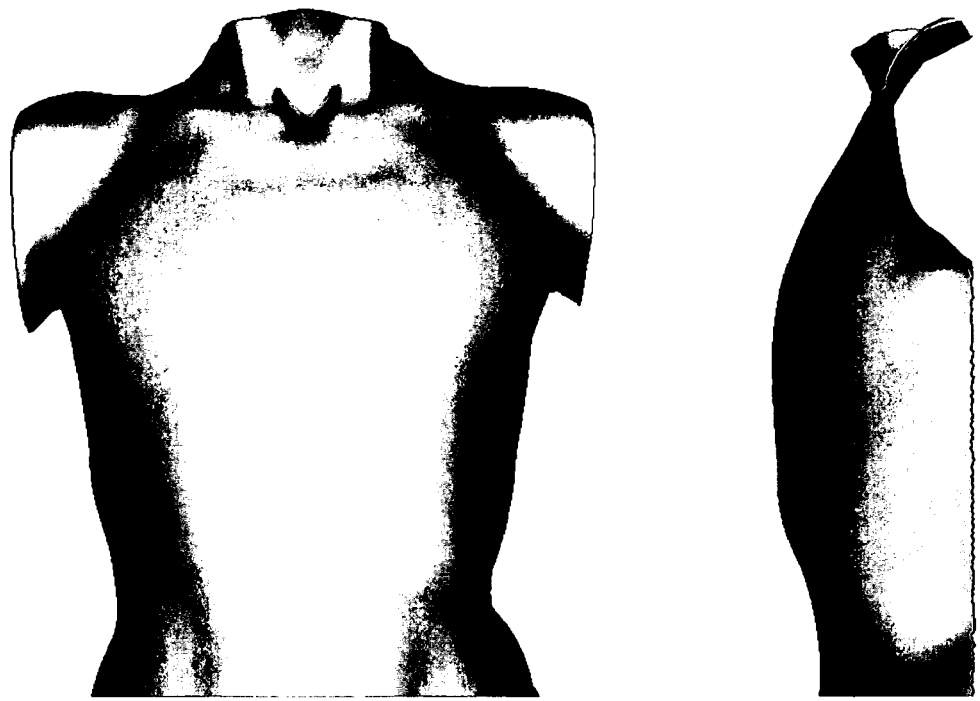
810          820
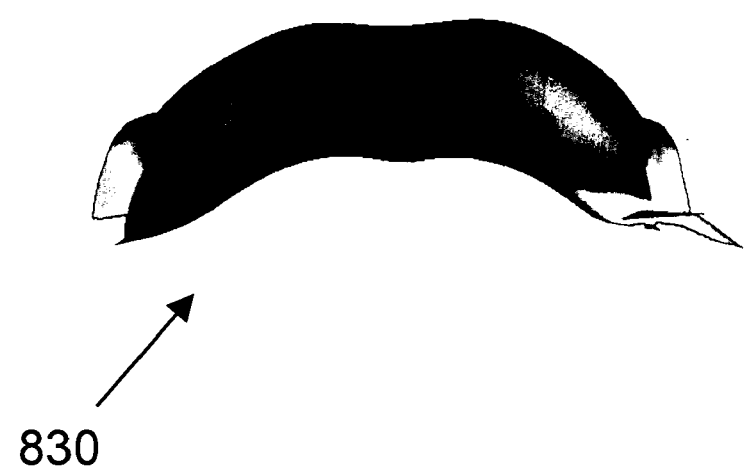
830

FIG. 11
1110 → nipples
1120 → areole
1130 → inframammary folds FIG. 14
1410
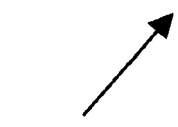
1420
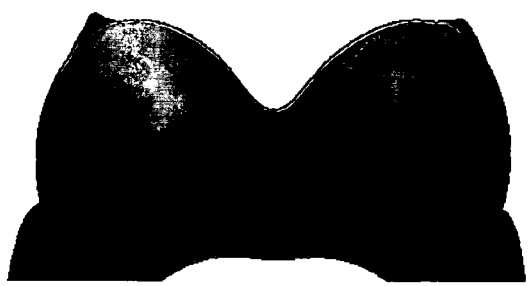
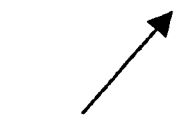
1430

ANATOMICAL RECOGNITION, ORIENTATION AND DISPLAY OF AN UPPER TORSO TO ASSIST BREAST SURGERY

CROSS-REFERENCE TO RELATED APPLICATIONS

This application is a continuation of U.S. patent application Ser. No. 13/644,744, filed Oct. 4, 2012, now issued U.S. Pat. No. 8,648,853, which is a continuation of U.S. patent application Ser. No. 12/319,639, filed Jan. 9, 2009, now U.S. Pat. No. 8,294,708, which claims priority to U.S. Provisional Application No. 61/010,591, filed on Jan. 9, 2008, the entire disclosure of each of these application being incorporated herein by reference.

BACKGROUND OF THE INVENTION

In most medical specialties, quantitative diagnostic imaging devices are utilized to assist physicians in diagnosis, operative plan development and postoperative analysis, offering accurate measurement and identification of possible complications. In breast augmentation and reconstructive surgery the main diagnostic tools utilized are the tape measure, calipers and camera in tandem with the physicians' "aesthetic artistry". Although successful, reoperative rates for breast augmentation have remained high.

With breast surgery being one of the most common surgical procedures and with the introduction of varied types of breast implants, some of which are in an anatomical form, there is a high likelihood of continued if not increased reoperative rates. There would be a benefit to having a diagnostic system that can precisely measure the critical dimensional parameters to identify possible regions of complications, identification of patient asymmetries, appropriate sizing and selection of breast implants and operative plan development, and postoperative analysis and documentation. The present invention addresses this need and advances the art by providing new techniques for automatic recognition of anatomical landmarks and features. It is directed to provide consistent and precise measurements between these locations, determination of the breast volumes and identification of asymmetries, such that they are incorporated in a device to assist breast surgery.

SUMMARY OF THE INVENTION

The present invention provides new techniques for automatic recognition of anatomical landmarks and features from a three-dimensional (3-D) representation of an upper torso. The various methods, techniques or modules in this invention allow for the automated analysis of the 3-D representation of the upper front torso (i) to recognize key anatomical features, (ii) to orient the subject with reference to their anatomy or a display, (iii) to determine dimensional analysis including direct point-to-point (linear) lines, 3-D surface lines, and volume values, (iv) to simulate the outcome with the addition of breast implants, (v) to assist in the selection of the breast implants, and/or (vi) to assist in the planning of breast surgery. The automated analysis is based on the analysis of changes in a 3-D contour map of the upper torso, orientation analysis of 3-D features and planes, color analysis of 3-D features, and/or dimensional analysis of 3-D features and positions of the upper torso.

In one embodiment, a computer-implemented method of determining a breast volume is provided. This is accomplished in an automatic fashion from a three-dimensional (3-D) representation of an upper torso. First a 3-D representation of a breast fold is recognized. The breast fold is defined as an unclosed curve along the 3-D surface of the 3-D representation defining the lower part of the breast. 3-D chest parameters are recognized from the 3-D representation, which are used to determine either a partial chest wall pertaining to the recognized breast fold or a chest wall including both sides of the chest (also referred to as a full chest wall). Examples of 3-D chest parameters are at least one anterior axillary line corresponding to the side of the recognized breast fold (at least two lines corresponding to the left and right breast fold when determining the volume of both breasts), an anterior chest midline, or a combination thereof.

The partial or full chest wall is optimized to features of a 3-D model of a chest wall. The breast volume of the original breast shown in the 3-D representation is determined from the recognized breast fold, the optimized partial or full chest wall and the 3-D surface integral of the 3-D representation of the upper torso. In case of determining the breast volume of both breasts (e.g. in one method step) the full chest wall could be used.

The 3-D representation of the upper torso could be modified by adding a 3-D resultant breast to the 3-D surface of either the partial or full chest wall. The 3-D resultant breast is defined herein as the sum of a 3-D breast implant volume and the originally determined breast volume multiplied by a factor (e.g. ranging from 0.3 to 0.6). The 3-D resultant breast is positioned near or at the bottom of the corresponding breast fold.

In another embodiment, a computer-implemented method of determining breast measurements is provided. Again, this is accomplished in an automatic fashion from a three-dimensional (3-D) representation of an upper torso. In one example of the automatic recognition of 3-D features, a contour analysis is performed to the recognized a first set of 3-D features and locations of the upper torso of the 3-D representation. This first set of 3-D features is then used to further recognize a second set of 3-D features and locations of the upper torso. In the recognition of the second of features, a contour analysis, a relational analysis of features, color analysis or dimensional analysis could be used either individually or in any combination.

Examples of the first set of recognized 3-D features and positions pertain to one or both nipples, one or more anterior axillary lines, the umbilicus, one or more facial features, or the neck, or any combination thereof. As indicated herein the 3-D representation of the upper torso could also be in color. Color information is for example useful in the recognition of the areola. Examples of the second set of recognized 3-D features and positions pertain to the sternal notch, the sternum, one or more clavicles, one or more chest wall parameters, an upper torso midline, a coronal plane, one or both areole, one or more breast fold lines, or one or more anterior axillary lines, or any combination thereof.

Using at least some of the recognized 3-D features and locations, a plurality of 3-D breast-related surface measurements can be determined in an automatic fashion. For example, one can determine a plurality of direct point-to-point breast-related distances or 3-D breast-related surface measurement.

Furthermore, planes and orientations with respect to the upper torso can be determined in automatic fashion using the recognized 3-D features. For example, the upper torso midline could be determined from at least one of the clavicles, the sternal notch, one or more of the breast fold lines, the sternum or one or more of the chest wall parameters. The coronal plane could be determined from at least one of the clavicles, the sternal notch, the upper torso midline, one or more of the axillary lines, one or more of the breast fold lines, the sternum or one or more chest wall parameters. In other words, the upper torso midline or the coronal plane of the upper torso could be defined by at least one of the second set recognized 3-D features and locations.

One example of a point-to-point breast-related distance is a first areola diameter in parallel to a transverse plane, whereby the transverse plane is defined as the plane orthogonal to both the coronal plane and the upper torso midline. Another example of a point-to-point breast-related distance is a second areola diameter parallel to the mid-sagittal plane, whereby the mid-sagittal plane is defined as the plane orthogonal to both the coronal and transverse planes.

The breast base width is yet another example of a point-to-point breast-related distance and corresponds to a breast fold of either the left or the right breast of the upper torso. In this determination, the breast fold is automatically recognized from the 3-D representation of the upper torso. The breast base width is the projection of the breast fold onto the coronal plane of the upper torso. In one variation, the breast base width could also be determined at the height of the superior boundary of the areola of either the left or the right breast of the upper torso. The breast base width is then the projection of a breast fold onto the coronal plane of the upper torso.

Other examples of direct breast related point-to-point distances are, but not limited to, a nipple-to-nipple distance, a nipple-to-midsternal line distance, an intermammary distance, a breast base width, one or more areola diameters, a mid-clavicle to nipple distance, a breast height, or a breast-fold line to projected position of the nipple onto a chest wall distance, or a combination thereof.

One example of a 3-D breast-related surface measurement is a breast fold corresponding to either the left or the right breast of the upper torso. The breast fold (also referred to as the breast fold line) is defined as an unclosed curve along the 3-D surface of the 3-D representation defining the lower part of the breast.

Other examples of 3-D breast-related surface measurement are, but not limited to, a nipple to breast fold 3-D surface line, a sternal notch to nipple 3-D surface line, a clavicle to nipple 3-D surface line, or a mid-clavicle to nipple 3-D surface line, or a combination thereof.

Another measurement that could be automatically determined from the 3-D measurements and 3-D features is a breast cup size. First one would recognize breast fold lines and 3-D nipple features corresponding to the left and the right breast of the upper torso. Then we determine the length of a bust curve in a bust plane, whereby the bust plane bisects the recognized nipples and is orthogonal to the coronal plane. Another length is determined which is referred to as the length of an inferior surface curve. The interior surface curve is defined as a 3-D surface curve through a plane inferior of the breast fold lines, whereby the inferior plane is approximately parallel to the transverse plane. The breast cup size is based on the difference between the bust curve length and the interior surface curve length. This difference could be looked up in a table that lists the difference in relation to breast cup size.

In yet another embodiment, a computer-implemented method of orientating and displaying a three-dimensional (3-D) representation of an upper torso is provided, which is useful for consistency and repeatability of measurements and recognition of 3-D representation(s).

Again, this is accomplished in an automatic fashion from a three-dimensional (3-D) representation of an upper torso. First, a plurality of 3-D features and locations of the upper torso from the 3-D representation of the upper torso. In addition, an upper torso midline is defined by at least one of the recognized 3-D features and locations. Furthermore, a coronal plane of the upper torso is defined by at least two of the recognized 3-D features and locations. The 3-D representation can then be rotated and displayed on a display such that the coronal plane of the upper torso coincides with the view plane of the display, and such that the upper torso midline is parallel to the vertical axis of the display.

In one embodiment regarding asymmetry analysis, one or more bisection lines can be recognized and displayed. Each of the lines bisects an anatomical feature or bisects two anatomical features of the same type (e.g. the nipple of the left or the right breast, the areole of the left or the right breast, or one or more breast fold lines of the left or the right breast). At least one of the bisection lines can be used as a measure of asymmetry of the anatomical feature pertaining to the left and the right breast. A transverse plane can be defined as the plane orthogonal to both the coronal plane and the upper torso midline, whereby the bisection lines can then be displayed parallel to transverse plane.

In another embodiment, a computer-implemented method of visually comparing different three-dimensional (3-D) representations of the same upper torso in an automatic fashion is provided. For a fust 3-D representation, a first set and a second set (as described supra) of 3-D features and locations of the upper torso is recognized. Then for a second 3-D representation, a first set and a second set (as described supra) of 3-D features and locations of the upper torso is recognized. Given these analyses, the first and the second 3-D representation are orientated towards each other by minimizing one or more of the differences in the respective 3-D positions and orientations between their respective first and second set of recognized features in the corresponding 3-D representations.

In still another embodiment, a computer-implemented method of determining a resultant three-dimensional (3-D) breast shape in an automatic fashion from a 3-D representation of an upper torso is provided. The determination of a resultant 3-D breast shape is based on the recognized breast folds, 3-D chest parameters and the optimized chest wall (partial or full). With these parameters and features, a resultant 3-D breast shape is added to the 3-D surface of the optimized chest wall. In this process, the lower boundary of the resultant 3-D breast shape is located near or at its respective breast fold line. Furthermore, the resultant breast shape is defined by width, height and projection parameters. The height is determined by a chest wall height or a breast fold line, or a combination thereof. The width is less than or equal to a breast base width. The projection is determined by a resultant breast volume of the resultant 3-D breast. The volume of the resultant 3-D breast shape is defined as the sum of a 3-D breast implant volume and an originally determined breast volume from the 3-D representation multiplied by a factor (e.g. ranging from 0.3 to 0.6).

In one aspect of this embodiment, the breast fold(s) could be moved in the inferior, superior, lateral or medial direction along the surface of the resultant 3-D breast shape or in any combination of the directions. The resultant 3-D breast shape is then added to the 3-D surface of the optimized chest wall, whereby the lower boundary of the resultant 3-D breast shape is located near or at its respective breast fold line, whereby the breast fold line is in the new and moved position.

In still another embodiment, a resultant 3-D nipple feature and position on the resultant 3-D breast can be automatically determined from the 3-D representation. In general, the resultant 3-D nipple feature and position is determined from an originally determined 3-D nipple feature and position in the 3-D representation. Like the breast fold line, the resultant 3-D nipple feature could be moved in the inferior, superior, lateral or medial direction along the surface of the resultant 3-D breast shape or in any combination of the directions. In addition, a resultant areola color and 3-D boundary on the resultant 3-D breast could be automatically determined. In this determination, the 3-D areola boundary containing the resultant 3-D nipple feature and position. Furthermore, the resultant 3-D areola color boundary could be determined from an originally determined 3-D areola boundary and color in the 3-D representation. Like the resultant breast fold and resultant nipple, the resultant 3-D areola color boundary could be moved in the inferior, superior, lateral or medial direction along the surface of the resultant 3-D breast shape or in a combination of the directions.

In still another embodiment, an automatic determination of a resultant nipple medial-to-lateral displacement on the resultant breast shape is provided. In this example, 3-D features and positions of an original nipple, an upper torso midline, a coronal plane and a transverse plane are recognized from the 3-D representation. A vector is then determined perpendicular to the chest wall bisecting the original nipple position, whereby the vector is in the transverse plane.

The resultant nipple medial-to-lateral displacement is defined as the intersection of the resultant breast shape with the vector in the transverse plane.

In still another embodiment, an automatic determination of a resultant nipple inferior-to-superior displacement on the resultant 3-D breast shape is provided. In this example, 3-D features and position of an original nipple and clavicle corresponding to the side of the nipple, an upper torso midline, a mid-sagittal plane from the 3-D representation. The distance between the nipple and clavicle is determined in a plane parallel to the mid-sagittal plane. The resultant nipple inferior-to-superior displacement is defined by preserving the distance between the nipple and the clavicle on the 3-D surface of the resultant 3-D breast shape within the plane parallel to the mid-sagittal plane.

The method to determine the resultant nipple superior displacement on the resultant 3-D breast shape can be varied by analyzing 3-D representations in different postures. For example, a second 3-D representation of an upper torso representing the upper torso with the hands elevated above the head compared to the original or first 3-D representation representing the upper torso with the hands in the proximity of the hips. For both 3-D representations, the breast fold(s), 3-D chest parameters, 3-D features of the nipples relative to the chest parameters from their respective 3-D representations are recognized. The resultant nipple superior displacement is defined as the difference between the nipple positions recognized in the (first or original) 3-D representation and the second 3-D representation.

BRIEF DESCRIPTION OF THE FIGURES

The present invention together with its objectives and advantages will be understood by reading the following description in conjunction with the drawings, in which:

FIG. 7 shows according to an embodiment of the present invention a 3-D representation of an upper torso in different views (frontal view 710, side view 720 and inferior to superior view 730).

FIG. 8 shows according to an embodiment of the present invention a 3-D representation of a virtual or determined chest wall in different views (frontal view 810, side view 820 and inferior to superior view 830).

FIG. 11 shows according to an embodiment of the present invention frontal plane views to determine asymmetries in, for example, the 3-D features of the nipples (shown in 1110), areole (shown in 1120) and the inframammary folds (shown in 1130).

FIG. 14 shows according to an embodiment of the present invention a 3-D representation of an upper torso in different views with a simulated resultant breast shape for the left and right breasts (frontal view 1410, side view 1420 and inferior to superior view 1430). These figures can be compared to the original 3-D representation prior to simulation as shown in FIG. 7.

DETAILED DESCRIPTION

Figure 1:
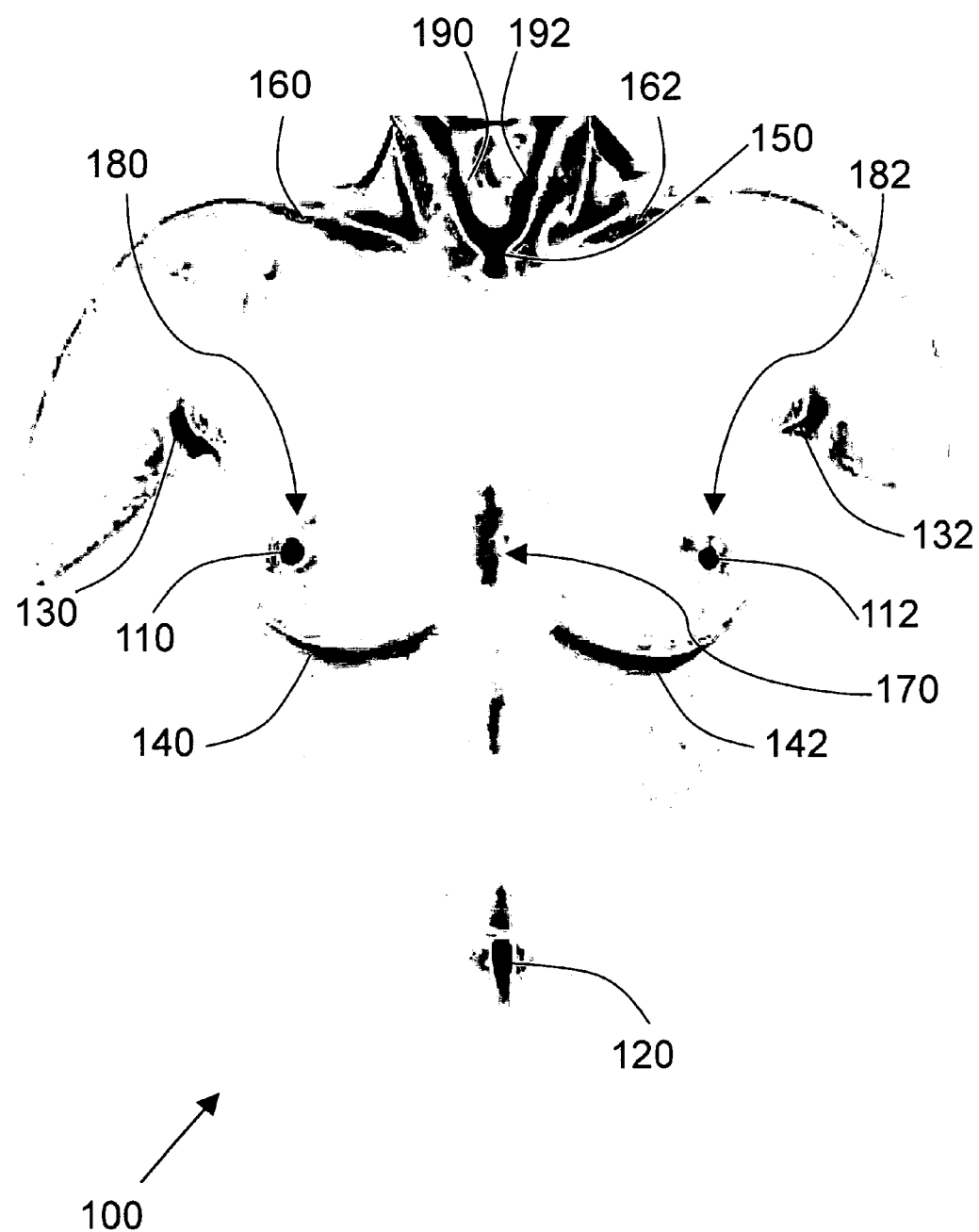
FIG. 1 shows according to an embodiment of the present invention a 3-D representation of an upper torso 100 (frontal view).

The invention is a computer-implemented method of analyzing in an automatic fashion a three-dimensional (3-D) representation of an upper torso. The 3-D representation is a 3-D contour representation of the upper torso, or its associated 4-D contour-color representation, which is the 3-D contour representation with photographic color applied to it. Herein the 3-D contour representation or the 4-D contour-color representation is referred to as the 3-D representation.

The 3-D representation can be generated with a variety of techniques and this invention is independent of the means of generation and/or capture thereof. The 3-D representation of the upper torso of the patient is preferably obtained with the patient in a specific (and preferably repeatable) position. In one example, this position reflects the patient positioned with their shoulders in a posterior direction, their shoulder blades as close as possible and their arms at their sides. For further consistency their hands may be positioned on their lateral thighs or on hand grips associated with a device. In addition footprints associated with the device may be incorporated to preferentially locate the feet. All such aspects of positioning assist in the orientation of the patient with respect to the device and to provide consistent measurements.

The various methods, techniques or modules in this invention allow for the automated analysis of the 3-D representation of the upper front torso (i) to recognize key anatomical features, (ii) to orient the subject with reference to their anatomy, (iii) to determine dimensional analysis including direct point-to-point (linear) lines, 3-D surface lines, and volume values, (iv) to simulate the outcome with the addition of breast implants, (v) to assist in the selection of said breast implants, and/or (vi) to assist in the planning of breast surgery.

Recognition of 3-D Features

The initial step is to perform a 3-D contour analysis on the 3-D representation of the upper torso. In one embodiment, 3-D features and locations are automatically recognized and analyzed from both the contours and the rate of change of the contours on the 3-D representation (e.g. 100, 200, 300 and 400 in FIGS. 1-4 respectively). For the purposes of illustration in this application, the examples shown in FIGS. 1-4 are in grey scale where the white regions have no or minimal rate of change, the grey regions have a rate of change reflected by the grey scale, and the black regions are maxima or minima. As a person of average skill in the art to which this invention pertains would readily understand is that color contour maps could also be used instead of grey scale contour maps. Examples of anatomical 3-D features and locations that can be automatically recognized are one or both nipples (110, 112), the umbilicus (120), axilla (130, 132), one or more axillary lines (also defined as the lateral part of the breast fold line; see 610 in FIG. 6, which also shows elevated arm 620), breast fold lines (140, 142), the sternal notch or head (150), one or more clavicles (160, 162), one or more chest wall parameters (discussed infra), an upper torso midline (170, i.e. the sternum; see also the midsternalline 510 in FIG. 5), a coronal plane (discussed infra), one or both areole (180, 182), the sternocleidomastoid muscles (190, 192), the neck (210), trapezius muscles (220, 310), features of the face (e.g. the mouth (410), the corners of the eyes (420, 422), the folds of the sides of the nose (430, 432), the chin (440), or the chin fold (442)). Other features not listed herein could also be recognized from the 3-D representation. Accordingly, the invention is not limited to these recognized features.

In another embodiment, a first set of 3-D features and locations is automatically recognized and analyzed from both the contours and the rate of change of the contours on the 3-D representation. In particular, at least one of the prominent anatomical 3-D features that are recognized are one or both nipples, the umbilicus, one or more features of the face, the neck, one or more breast fold line, one or more (anterior) axillary lines, or any combination thereof.

Once at least some of the first set of 3-D features is recognized, other 3-D features (referred to as the second set) can be recognized from the 3-D representation using in one example at least one or more of the first set of recognized features as a guideline. Examples of the second set of 3-D features and locations are the sternal notch, one or more clavicles, one or more chest wall parameters, an upper torso midline (i.e. the sternum), a coronal plane, a sagittal plane, a transverse plane, one or both areole, one or more breast fold lines, or one or more interior axillary lines.

Three major (coronal, sagittal and transverse) planes through the upper torso, and the inferior, superior, medial, lateral, anterior and posterior directions are defined according to anatomical nomenclature, which are automatically recognized. In the 3-D representation, the 3-D convex features of the upper torso could be associated with the clavicles. The coronal plane could then be defined by two lines such as: (i) a fitted line through the left and right clavicles, and (ii) the upper torso midline (see also infra). The transverse plane is defined as the plane orthogonal to both the coronal plane and the upper torso midline. The remaining sagittal plane is parallel to upper torso midline and orthogonal to both the coronal and transverse planes.

The orientation aspects of the upper torso can be automatically defined, for example in one exemplary embodiment, by recognizing anatomical features and comparing their location to a reference, such as the image illustrated in FIGS. 1-4. For example, if the umbilicus defines a feature that is inferior to most other features it defines the inferior direction from the center of the 3-D representation. An alternative approach is to transform the camera frame of reference 3-D representation to a reference frame determined in the calibration of the system or at the point of design, which is not exactly the anatomical frame of reference. For the purposes of this invention, inferior-superior direction is defined within the coronal plane parallel to the upper torso midline, and has directionality from the umbilicus to nipples to sternal notch and neck. Medial to lateral is defined within the coronal plane and is perpendicular to the upper torso midline and has directionality from midline to nipples to axillae. Posterior to anterior is defined within the transverse plane and is perpendicular to the upper torso midline and has directionality from sternal notch to nipples.

In general, the rate of change in contours can be calculated from the 3-D representation for each point as the difference in x, y, z in nearby coordinates or their equivalents. Typically for the upper front torso this yields two prominent local maxima and four prominent local minima. Where usually, these maxima are recognized as the nipples. The umbilicus, sternal notch and axillae are recognized as the minima. A detailed set of criteria can be utilized to recognize the 3-D features.

For example, a nipple can be recognized in the 3-D contour rate of change analysis as being a local maximum, with a large rate of change in all radial directions with the centers as the maxima over a small region of about 8 to 15 mm in diameter. For the upper torso, the nipples usually are the two regions with the greatest rate of change in contours that are maxima. The two nipples are recognized and they are separated by approximately equal to or greater than 15 cm. Other criteria maybe used to further confirm recognition of the nipples, such as confirming that they lie within a region that has a darker color than the average skin color in the 3-D representation.

The umbilicus is recognized in the 3-D contour rate of change analysis as having a local minimum, with a large rate of change in all radial directions with the centers as the minimum from this center over a small region of about an oval or circular region with major and minor axis varying from approximately 10 to 30 mm, respectively. For the upper torso, the umbilicus usually is the region with the greatest rate of change in contours that is a minimum.

Figure 3:
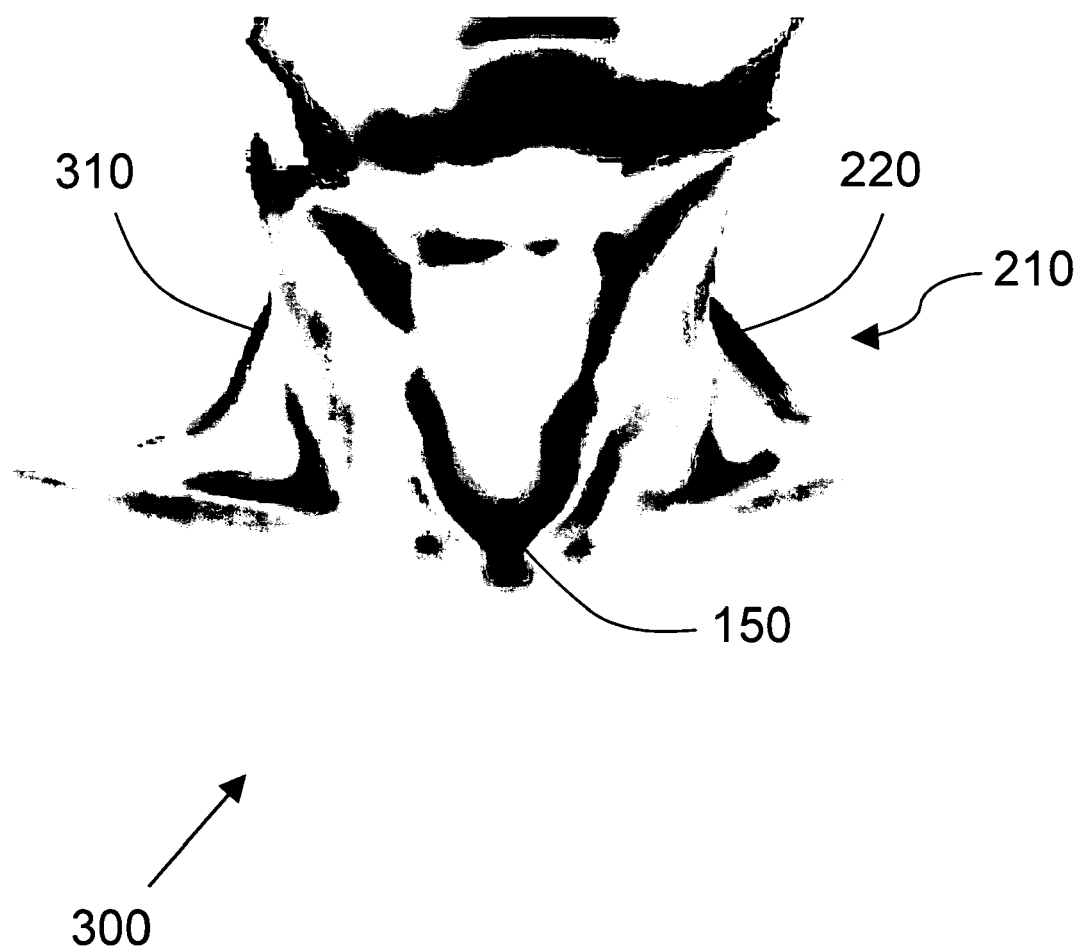
FIG. 3 shows according to an embodiment of the present invention a 3-D representation of a neck 300 (frontal view).
Figure 4:
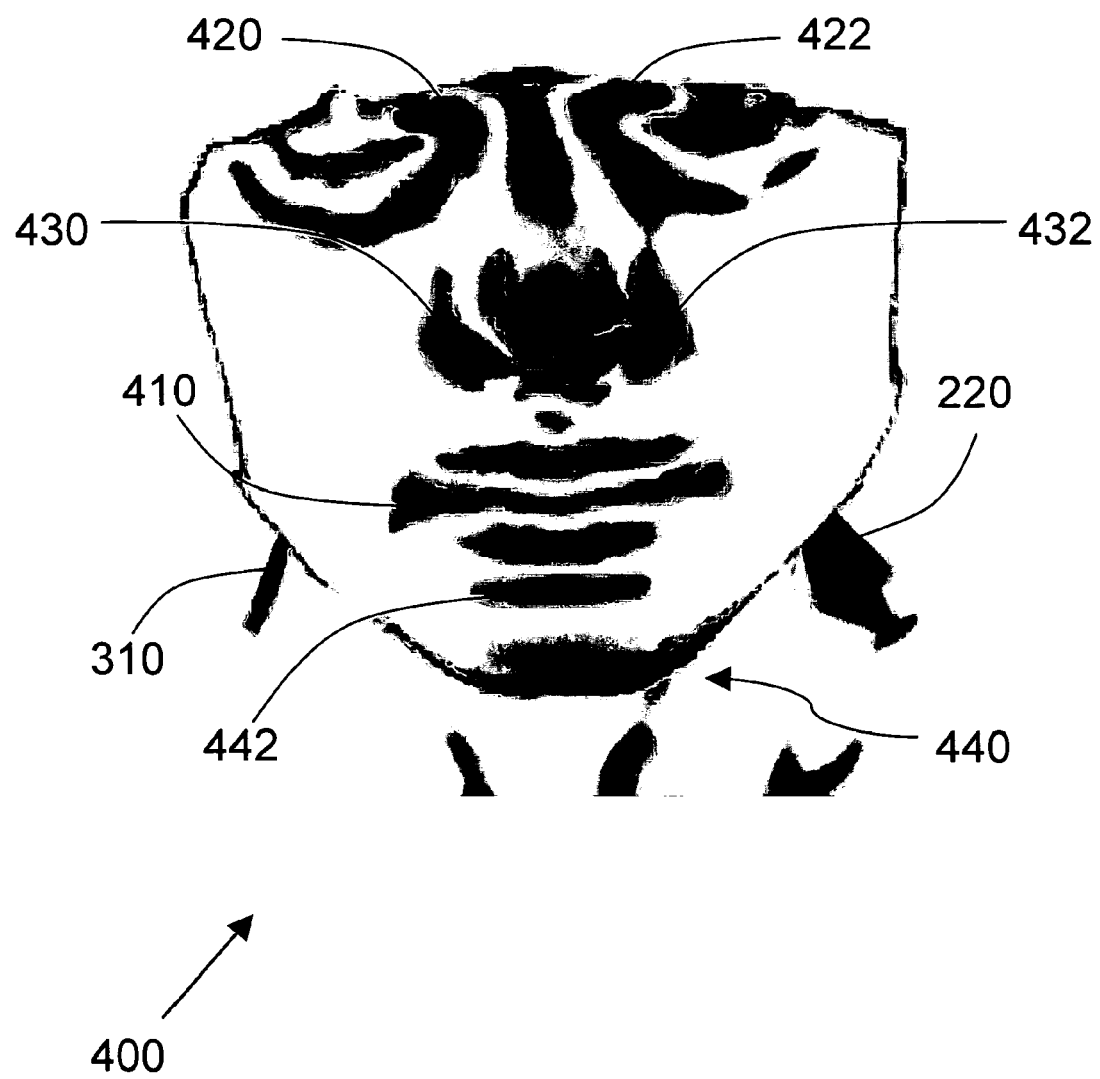
FIG. 4 shows according to an embodiment of the present invention a 3-D representation of a face 400 (frontal view).

The face has many 3-D features present such as the chin, lips, nose and eyes, which can all be recognized as prominent maxima when looked at with the contour rate of change analysis (see FIGS. 3-4). Even if only the lower part of the face is included in the 3-D representation it is distinct because of the general surface shape is oval down to the chin and there are many prominent features that are maxima and regions of convexity in close proximity to each other. The chin ridge line defining the jaw line is distinctive. In general, the face can be recognized with the chin and neck defining the superior part of the torso.

Figure 5:
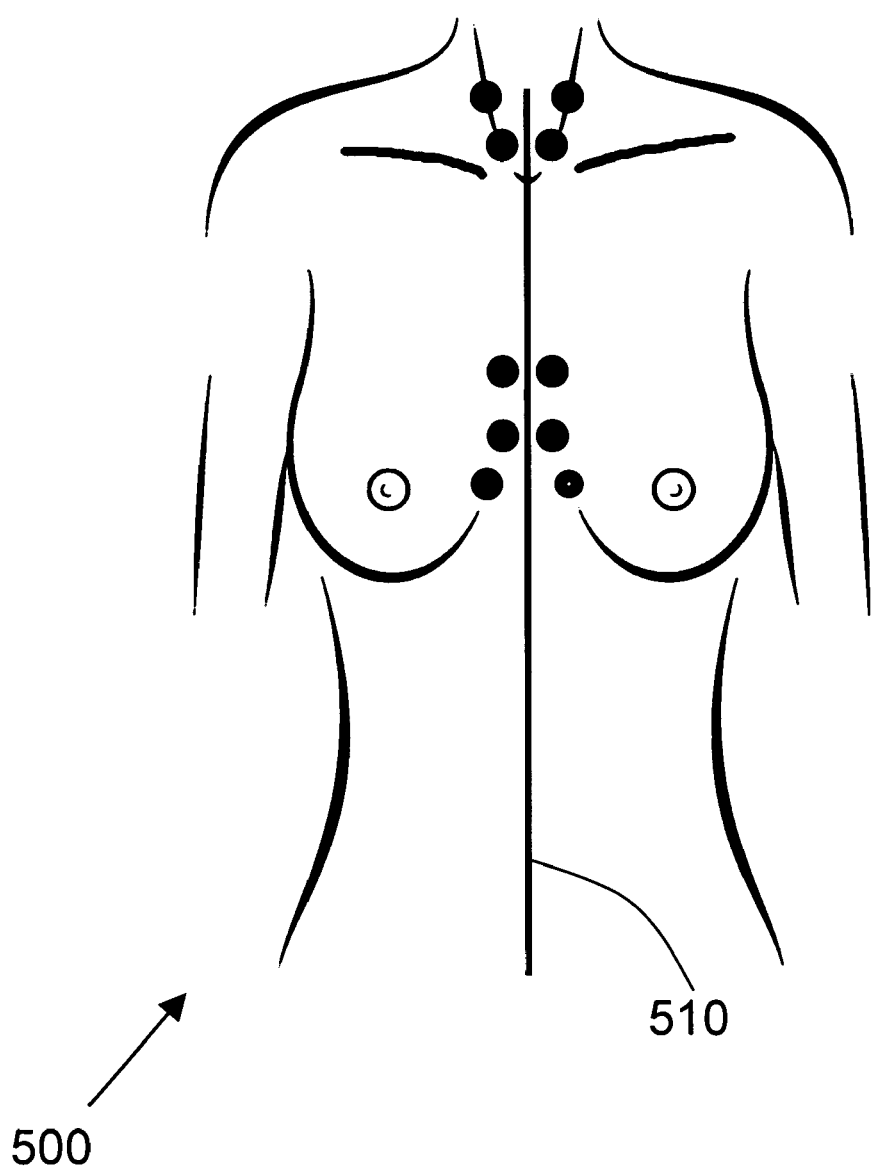
FIG. 5 shows according to an embodiment of the present invention a frontal view 500 of the upper torso indicating a torso midline 510.
Figure 6:
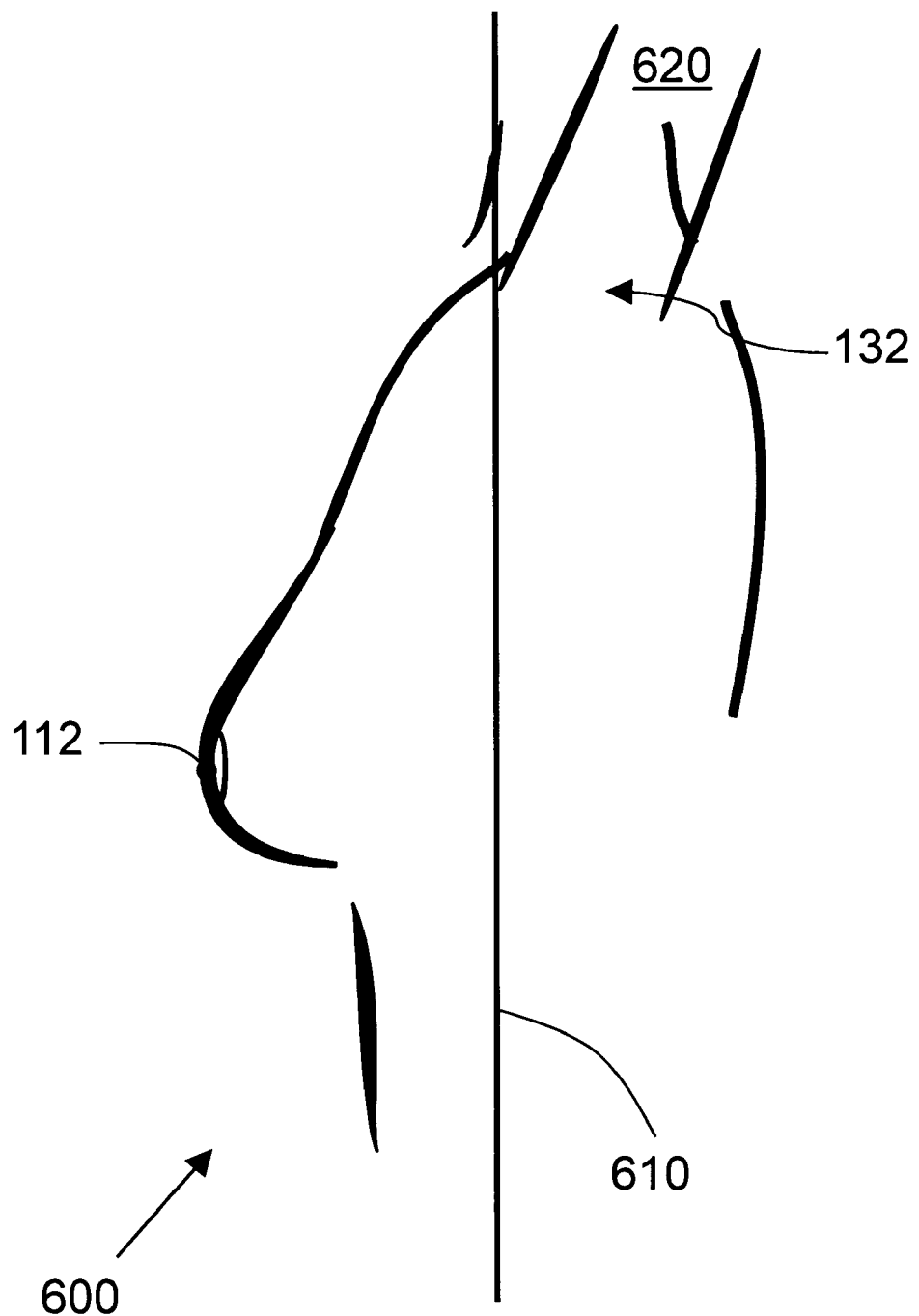
FIG. 6 shows according to an embodiment of the present invention a side view 600 indicating an axillary line 610.

The neck is recognized in the 3-D representation as being the narrowest region of the torso i.e., shortest distance between two boundaries (see FIGS. 1-4). An additional criterion that can be used to differentiate the neck from the surface of the arms and legs is that the neck is in close proximity to the chin. Moreover, the neck has distinctive 3-D features when looked at with the contour rate of change analysis. The chin defines a ridge of convexity (line of maxima). The sternocleidomastoid muscle defines two prominent convex ridges on the neck's surface defining the anterior triangle of the neck, which surrounds a local minima and region of concavity defining the sternal notch. Lateral to either side of the anterior triangle of the neck are the triangles concave structures that are also present in the contour rate of change analysis. These are anatomical features for the trapezius muscles and which are inferiorly bounded by convex ridges of the clavicles. The sternal notch location could be fine-tuned or refined as the bisection of this midline and a curve fit to the convex ridges lateral to the neck associated with the clavicle geometry, as shown in FIGS. 1 and 5. Moreover the sternal notch is the local minimum in a posterior direction closest to the intersections of the midline and clavicle fitted curves.

An individual breast fold line is recognized in the 3-D representation. The breast fold line is the line of transition between the convex breast and the concave regions adjacent to the breast. Breast fold lines could be further refined with the knowledge of the nipple locations. The search region could then be restricted to radial distances from the nipple of about 3 to 15 cm rather than the entire upper torso. In one exemplary embodiment and for the purposes of further analysis in this invention, the breast fold line is defined as an unclosed curve along the 3-D surface of the 3-D representation defining the lower part of the breast.

The axillae are determined with the knowledge of additional 3-D features, such as breast fold lines and the upper torso orientation. In one example, an axilla could be found as the local minimum superior and lateral to the lateral boundary of the breast fold line. The areole could be determined using the color boundary information and nipple location recognized in the 3-D representation.

The lower torso midline is also visible in the contour rate of change analysis, however, it is noted that our analysis derives the upper torso midline; as such the lower torso midline and position of the umbilicus may not correspond to the appropriate line. To determine the upper torso midline, we examine at least two regions: the medial region between the breast folds superior to the height of the nipples and the medial region of the neck and more specifically the anterior triangle of the neck, as shown in FIGS. 1-3 and FIG. 5 (indicated by the black dots). In the medial region superior to the height of the nipples between the upper breast fold lines, data from the fold lines themselves and local contour are reviewed to determine the system plane between left and right sides of the chest wall. Likewise for medial region of the neck with the lower left and right convex features associated with the sternocleidomastoid muscles. The upper torso midline is determined by fitting the line through the middle of these points.

Virtual Chest Wall

This invention includes constructing a virtual chest wall (whereby the soft tissue envelope may be included or excluded) and subtracting the patient's 3-D contour surface. A key assumption in this method is that the breast tissue (including parenchyma and soft tissue envelope) is positioned on the anterior chest wall. In one exemplary embodiment, the chest wall under the breasts can be approximately described by the following anatomical features and analyses.

Figure 2:
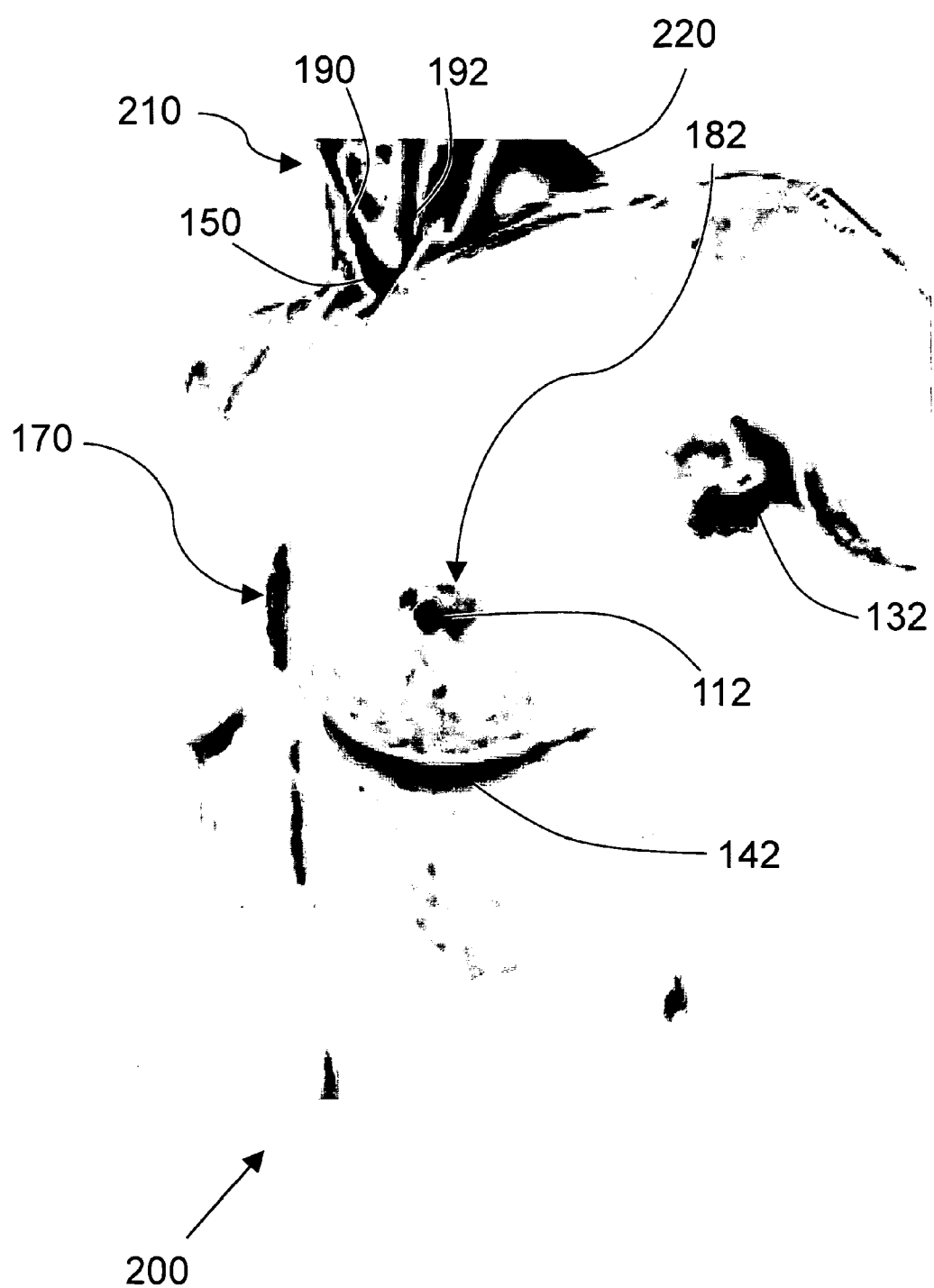
FIG. 2 shows according to an embodiment of the present invention a 3-D representation of an upper torso 200 (front-side view).

The breast fold line which determines the boundary of the breast tissue, as illustrated in FIGS. 1-2. The chest near the breast folds is approximately a curved line surrounding the breast and is determined where the distance is about 1 cm radially beyond the breast fold line;

The chest wall's medial curvature in the sagittal plane which is defined by the sternum curvature along the upper torso midline;

The breast fold lines for both sinister and dextro define the respective lateral lines of curvature of the chest wall (also referred to as the axillary lines); and To compensate for the presence of the pectoral muscle the axillary crease horizontal line is obtained from just inferior of the axilla and bisects the breast fold line to the upper torso midline. This line also does not have to be a horizontal line, as long as it connects with the anterior axillary line and can take a more curved route to the midstemal line.

Figure 9:
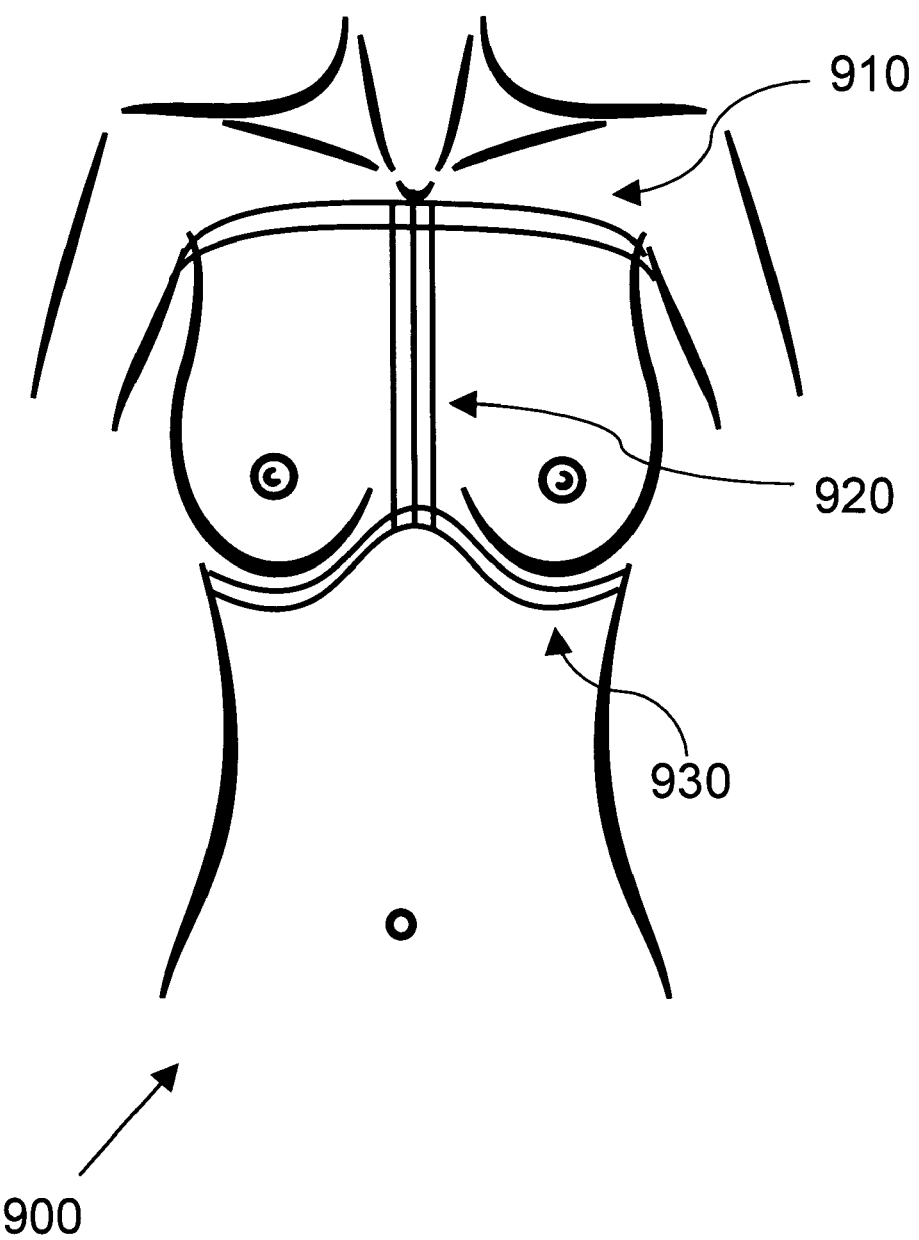
FIG. 9 shows according to an embodiment of the present invention a frontal view 900 with chest wall line that are used as chest wall parameters.

FIG. 8 shows examples 810, 820, and 830 of the virtual chest wall in different view planes, which is defined with these lines of curvature and can be created utilizing spline interpolation or fitting to a functional form (e.g. a model of a chest wall, e.g. as shown in FIG. 7) or a combination of both techniques. To improve the anatomical accuracy and continuity between the virtual chest wall with the exposed chest wall, another method for use of spline interpolation is to have more than one curve (910, 920, 930) enclosing the breast tissue, as shown in FIG. 9. These lines of curvature along the chest wall contain information relating to the chest wall and are referred to as the chest wall parameters.

Measurements

The feature recognition of the 3-D representation allows one to further automatically calculate breast-related direct point-to-point distances, 3-D surface measurements (3-D lines), which are useful to assist in breast imaging, analyses of breast implants and sizing, analyses of asymmetries, and breast surgery planning. The following is a description of such measurements and how they are automatically determined (reference for these measurements can be made to FIGS. 1-8).

Point-to-Point Distances

Breast base width. In one example, breast base width corresponding to a breast fold of either the left or the right breast of the upper torso is determined as the projection of the breast fold line onto the coronal plane of the upper torso. In another example, breast base width is determined at the height of the superior boundary of the areola of either the left or the right breast of the upper torso. The breast base width is the point-to-point distance between the lateral and medial sides of the projection of a breast fold onto the coronal plane of the upper torso at the appropriate height.

Nipple to Midsternal Line.

The linear measurement of the nipple to midsternal line is determined as the shortest distance between the 3-D coordinates for the nipples and the midsternal line.

Areola Diameters.

The recognition of areole is determined using the color boundary information and nipple location recognized in the 3-D representation. The area at which the color darkens from the surrounding tissue is the resulting color boundary of the areola. The areola is typically round in appearance, but our measurements of the 3-D representation determine a general round shape. The nipple 3-D feature is contained within the areola boundary, with the nipple generally located at the center of each areole. Two areola diameter measurements maybe determined for each areola, one parallel to the transverse plane and the second parallel to the midsagittal plane, wherein the diameter measurement is a point-to-point measurement from one edge of the boundary to the other edge of the boundary of the same areola.

Nipple to Nipple Distance.

The linear measurement between the two nipple positions is calculated as the shortest distance between the 3-D coordinates of the left and right nipples.

Intermammary Distance.

The linear measurement of the intermammary distance is calculated as the shortest distance between the 3-D coordinates of the medial boundaries of both breast base fold lines corresponding to the left and right breast.

Breast-Fold Line to Projected Position of the Nipple onto a Chest Wall Distance.

The linear measurement of the breast fold line to the projected position of the nipple into the chest wall is calculated as the shortest distance between the most inferior point on the breast fold line to the projection of the nipple onto the virtual chest wall on the left side and similarly for the right side.

Mid-Clavicle to Nipple Distance.

The linear measurement of the mid-clavicle to nipple distance is calculated as the shortest distance between the center point of the clavicle on the left side to the left nipple and similarly for the right side.

Breast Height.

The linear measurement of the breast height is calculated as the shortest distance between the horizontal line that is obtained from just inferior of the axilla and bisects the breast fold line to the midsternal line (this does not have to be a horizontal line as long as it connects with the anterior axillary line and can take a more curved route to the midsternal line) and the most inferior point of the breast fold line.

Surface Measurements

3-D Sternal Notch to Nipple Distance.

The 3-D surface measurement of the sternal notch to nipple is calculated as the 3-D line integral over the patient's 3-D contour surface along the vector defined between the 3-D coordinates for the sternal notch and the nipple.

3-D Nipple to Breast Fold Distance.

The 3-D surface measurement of the nipple to inframammary or breast fold is calculated as the 3-D line integral over the patient's 3-D contour surface along the vector defined as the 3-D coordinates from the nipple to the inframammary breast fold line with the vector being parallel to the midsagittal plane.

3-D Clavicle to Nipple Distance.

The 3-D surface measurement of the clavicle to nipple is calculated as the 3-D line integral over the patient's 3-D contour surface along the vector parallel to the mid-sagittal plane that bisects the nipple. The 3-D distance is determined as the 3-D line integral between the nipple and the clavicle.

3-D Mid-Clavicle to Nipple Distance.

The 3-D surface measurement of mid-clavicle to nipple is calculated as the 3-D line integral over the patient's 3-D contour surface along the vector defined between the 3-D coordinates for the center point of the clavicle and the nipple.

Breast Cup Size

Figure 10:
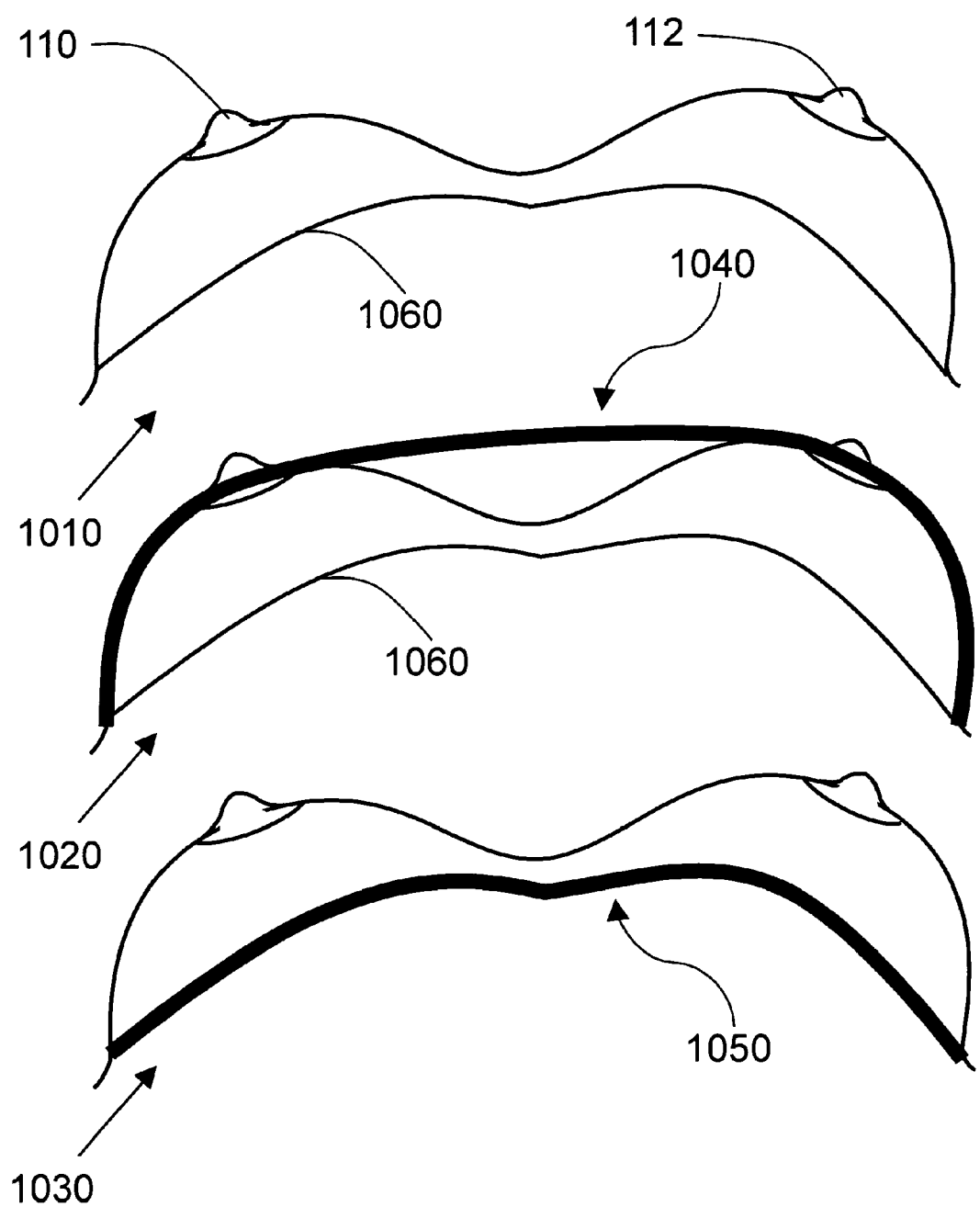
FIG. 10 shows according to an embodiment of the present invention views in the transverse plane of a breast outline (shown in 1010) that is used to calculate the length of a bust curve length (shown in 1020) and the length of an interior surface curve (shown in 1030).

Breast (also referred to as bra) cup size could be determined in an automatic fashion from the 3-D representation of the upper front torso. First, the breast fold lines and 3-D nipple features are recognized corresponding to the left and the right breasts. A plane is then defined that contains the nipples and which is orthogonal to the coronal plane. FIG. 10 shows the bust curve which determines the intersection of the 3-D representation of the upper front torso bisected by the bust plane, whereby the bust curve starts lateral for the breast fold line and follows the intersection of the 3-D representation and the plane to the region of a nipple, at which point the bust curve is linear from one nipple to the other nipple, then follows the intersection of the 3-D representation and the plane to a point which is lateral to the breast fold line. The length of the bust curve is determined (thick line 1040 in FIG. 10). A second curve is defined as the inferior surface curve (thick line 1050 in FIG. 10), wherein a 3-D surface line through a plane inferior of the breast fold lines, whereby the plane is approximately parallel to the transverse plane or the bust plane. The length of the inferior surface curve is determined, commencing and terminating at points along the surface curve (i.e. chest plane 1060) which are parallel to the coronal planes that bisects the commencing point and terminating points on the bust curve. The difference between the bust curve and inferior surface curve measurement yields a value, which by referring to saved tables of values yields a bra cup size.

Orientation, Display and Asymmetries

It is noted that difference can be observed in the midlines for the upper and lower torso as well as other regions of the body have also different midlines. The midline is a key component in deriving the anatomical coordinate system and the corresponding coronal, sagittal and transverse planes. For breast augmentation the upper torso midline and associated planes are appropriate. Displaying the torso with respect to these planes has benefits rather than in the native camera or other frame of reference.

Informative views of the front, oblique, profile, worm's eye and bird's eye views of the 3-D representation with the torso aligned with the midline in the vertical or horizontal axes can be generated in an automated fashion.

Figure 12:
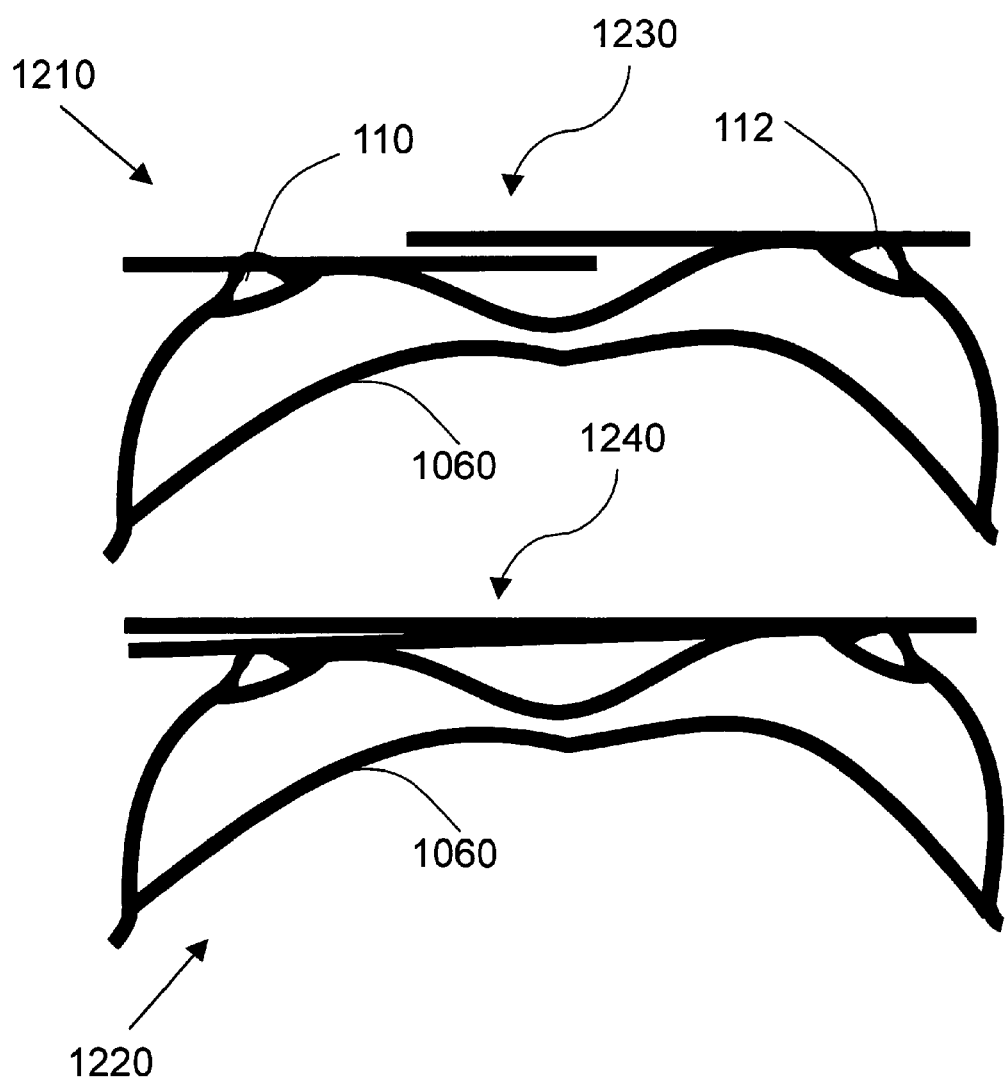
FIG. 12 shows according to an alternate embodiment of the present invention transverse plane views (1210 and 1220) to determine asymmetries in, for example, the 3-D features of the nipples.

If the 3-D representation is orientated and displayed such that coronal plane is parallel with the viewing plane and the 3-D representation is further orientated such that the midline is parallel to the vertical axis of the display, asymmetries become apparent. The preferred embodiment for analysis of the asymmetries of left and right anatomical features of the same type on the 3-D representation are horizontal lines parallel to the transverse plane displayed bisecting the anatomical features of interest. FIG. 11 exemplifies this for the anatomical features of the nipple of the left or the right breast, the areola of the left or the right breast, or inferior boundary of the breast fold lines of the left or the right breast. The extent of asymmetry can be determined by the minimum distance between the bisecting lines in the viewing plane, in this case the coronal plane. FIG. 12 demonstrates a nipple projection asymmetry by displaying the 3-D representation orientated with the transverse plane parallel to the viewing plane and the midsagittal plane parallel to the vertical axis. Two horizontal lines (1230) in the coronal plane are displayed each bisecting respective nipple locations (110, 112). The vertical difference in the horizontal lines is the degree of asymmetry in projection. In another embodiment, the asymmetries can be derived as an angular measurement 1240, e.g. the angle relative to the transverse plane, of a line between both nipples, between both areole, or between two breast folds projected onto the coronal plane (not shown).

Figure 13:
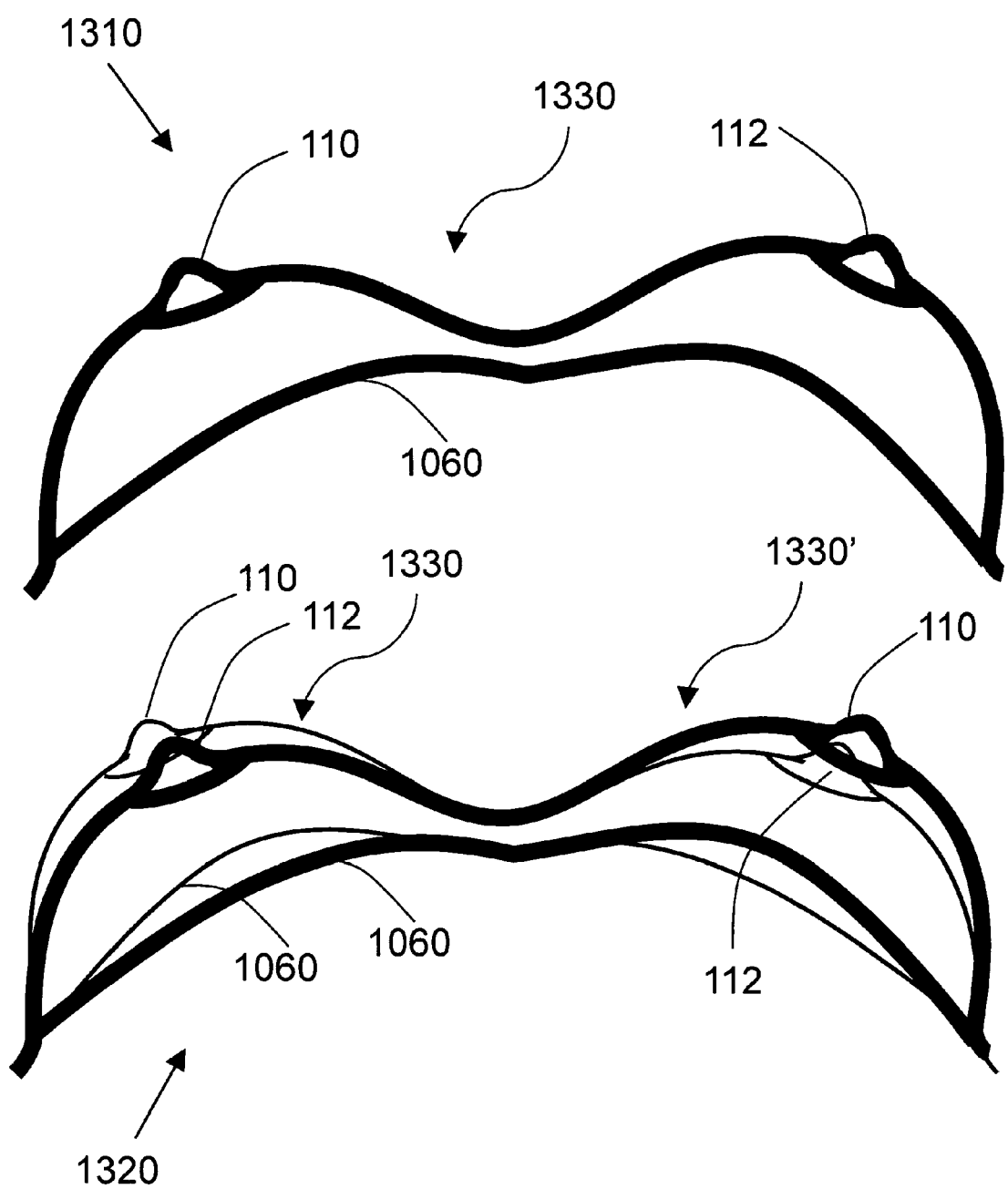
FIG. 13 shows according to an alternate embodiment of the present invention transverse plane views (1310 and 1320) to determine asymmetries in, for example, the 3-D features of the nipples.

FIG. 13 shows another form of displaying asymmetries with respect to the chest wall 1060 with a "worm's eye" view, i.e., the view from inferior to superior with the viewing plane parallel to the transverse plane. In this embodiment the chest parameter line inferior to the breast fold line is displayed and the breast projecting surface is outlined 1330. These two lines maybe reflected about the mid-sagittal plane such that the asymmetry of the breast projection and the underlying chest wall can be observed. This is shown by flipping 1330 from left to right resulting in 1330' and overlaying 1330 and 1330' (note that nipples 110, 112 are mirrored for 1330' compared to 1330). If there is a large change in chest wall with the reflection then, the asymmetry originates in the hard tissue. If there is a large asymmetry in breast projection and not in the chest wall, then the asymmetry originates in the soft tissue.

Breast Volume

Breast volume is determined for an individual breast or for both breasts in a single method step. The technique to determine breast volume requires recognizing the breast folds defining the lower part of the breasts from the 3-D representation, the 3-D chest parameters and the virtual chest wall as discussed supra. The volume of each breast is the 3-D integral between the two surfaces. Specifically, the 3-D integral of the 3-D representation and the virtual chest wall in the region of the specific breast described by the chest parameters.

Regarding, the breast volume for an individual breast one requires only the associated single breast fold, chest parameters around the single breast fold and a virtual chest wall that could either be a partial chest wall or the chest wall including the other breast's 3-D feature. In other words, the volume of the individual breast is then the 3-D integral between the 3-D representation and the partial virtual chest wall or virtual chest wall representation with the left and right side of the chest.

Simulation

The automated recognition of the 3-D features provides a platform to perform simulations of the resultant breast shapes and positions with respect to the virtual chest well as well as nipple position on the resultant breast shapes. The simulated outcomes can further assist in breast imaging, analyses of breast implants and sizing, analyses of asymmetries, and breast surgery planning.

Simulated 3-D forms simulating the outcome with the addition of breast implants and associated surgery to the existing (also referred to as original—see e.g. FIG. 7 which is the original 3-D representation) form in the 3-D representation creates resultant breasts (FIG. 14). The calculated 3-D resultant breast is positioned on the 3-D virtual chest wall (FIG. 8 which is the 3-D determined chest wall of FIG. 7) such that the inferior posterior boundary of the resultant breast shape is located on or near the breast fold line (e.g. 140, 142). The resultant breast has a 3-D resultant breast shape that has a height, width and projection. The volume of each resultant breast shape is equal to the implant volume plus the volume of the existing breast form with some degree of atrophy. The degree of atrophy reduces the existing breast volume by a factor (e.g. in the range of 0.3 to 0.6).

The location of the breast fold lines could be moved in the inferior, superior, lateral or medial direction along the surface of the resultant 3-D virtual chest wall or in any combination of these directions. The 3-D resultant and simulated breast is updated with the 3-D resultant breast shape translated so that it corresponds with the translation in the breast fold line.

In another aspect of the simulation, the resultant 3-D location of the nipple could be determined. In this case, the resultant 3-D simulation is the resultant 3-D breast shape positioned on the virtual chest wall, with the addition of the 3-D nipple feature added at the location of the nipple. The resultant 3-D nipple feature is equal to the original 3-D nipple feature in the original 3-D representation. Furthermore, the 3-D representation of the areola and the nipple feature on the original 3-D representation could be added to the 3-D simulation with the resultant 3-D breast shape at the determined location of the resultant 3-D nipple. Moreover, the color of the areola and nipple from the original 3-D representation could be added to the simulated outcome.

The resultant location of the nipple is dependent on the original location of the nipple recognized in the 3-D representation. Like the breast fold line, the resultant nipple position could also be adjusted in the superior, inferior, lateral, medial, or in any combination of these directions.

The resultant 3-D position of the nipple can be determined in a variety of ways. For example, the displacement of the resultant nipple from the original nipple position could be determined along two directions, i.e. the direction medial-to-lateral and the direction inferior-to-superior.

Figure 15:
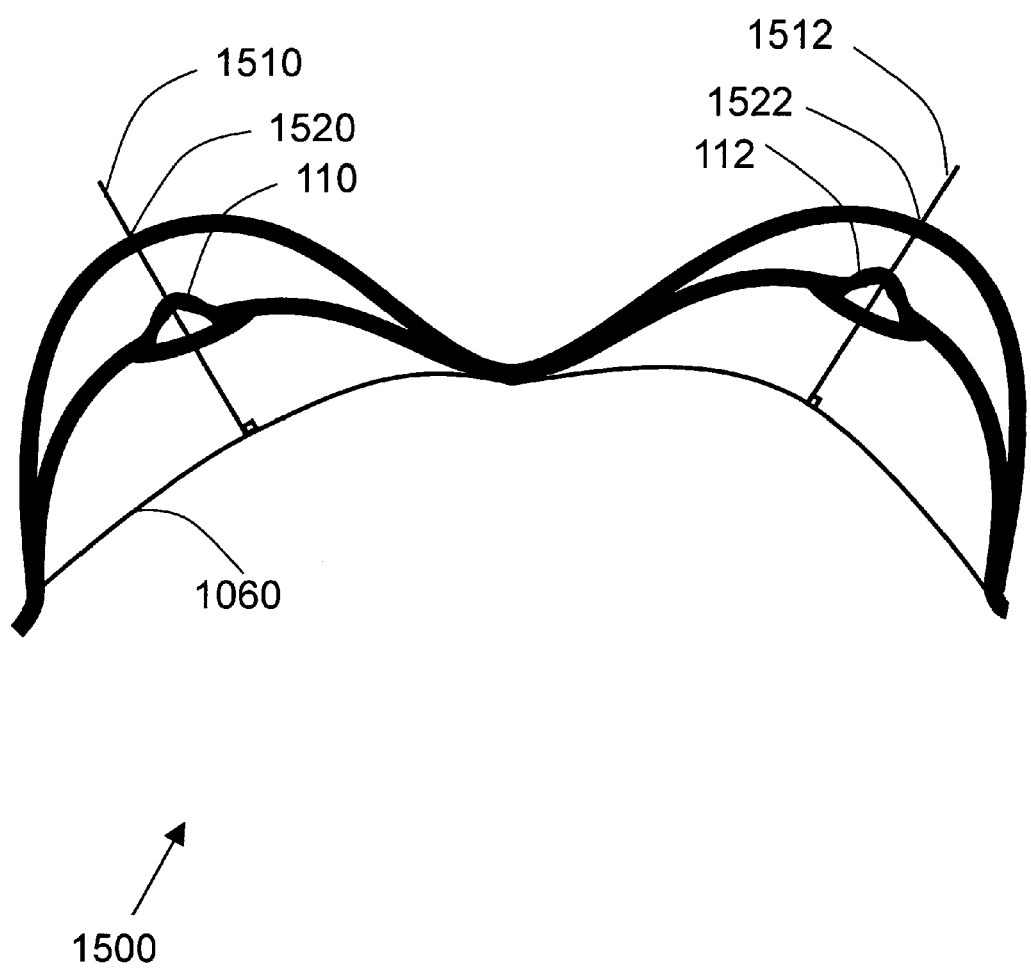
FIG. 15 shows according to an embodiment of the present invention a transverse plane view 1500 of a resultant nipple position with displacement in medial to lateral direction.

FIG. 15 shows the resultant nipple medial-to-lateral displacement on the resultant breast shape by determining a vector 1510, 1512 perpendicular to the chest wall 1060 bisecting the original nipple position 110, 112. This vector is in defined in the transverse plane. The resultant nipple position 1520, 1522 is the point of intersection of the vector with the resultant breast shape.

Figure 16:
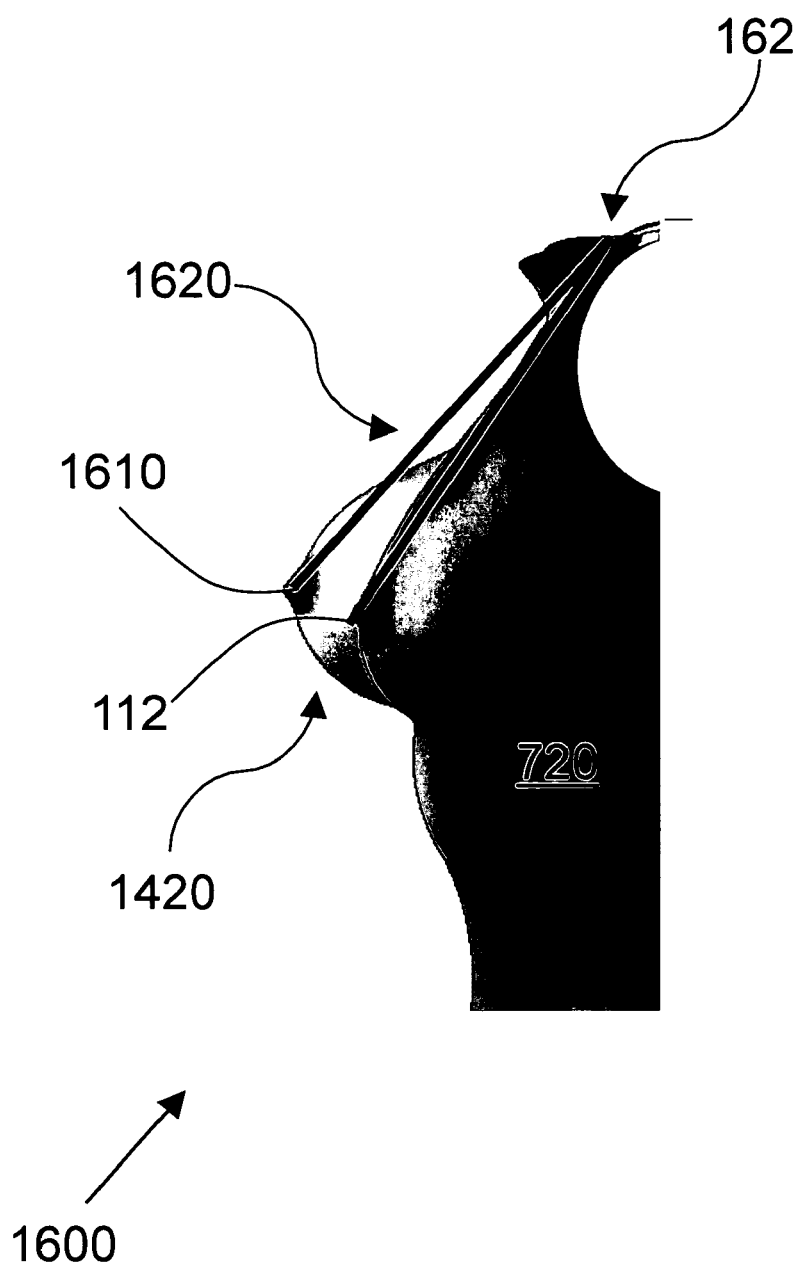
FIG. 16 shows according to an embodiment of the present invention a side view 1600 of a overlapping 3-D presentations 720 and 1420 used to determine a resultant nipple position with displacement in interior to superior direction.

FIG. 16 shows the resultant nipple inferior-to-superior displacement 1610 on the resultant breast shape (1420) by determining the distance 1620 between the nipple 112 and the clavicle 162 in a plane parallel to the mid-sagittal plane on the original 3-D representation 720, while preserving the distance between the nipple and the clavicle on the 3-D surface of the resultant 3-D breast shape within a plane parallel to the mid-sagittal plane (i.e. the two lines 1620 are of constant length).

Figure 17:
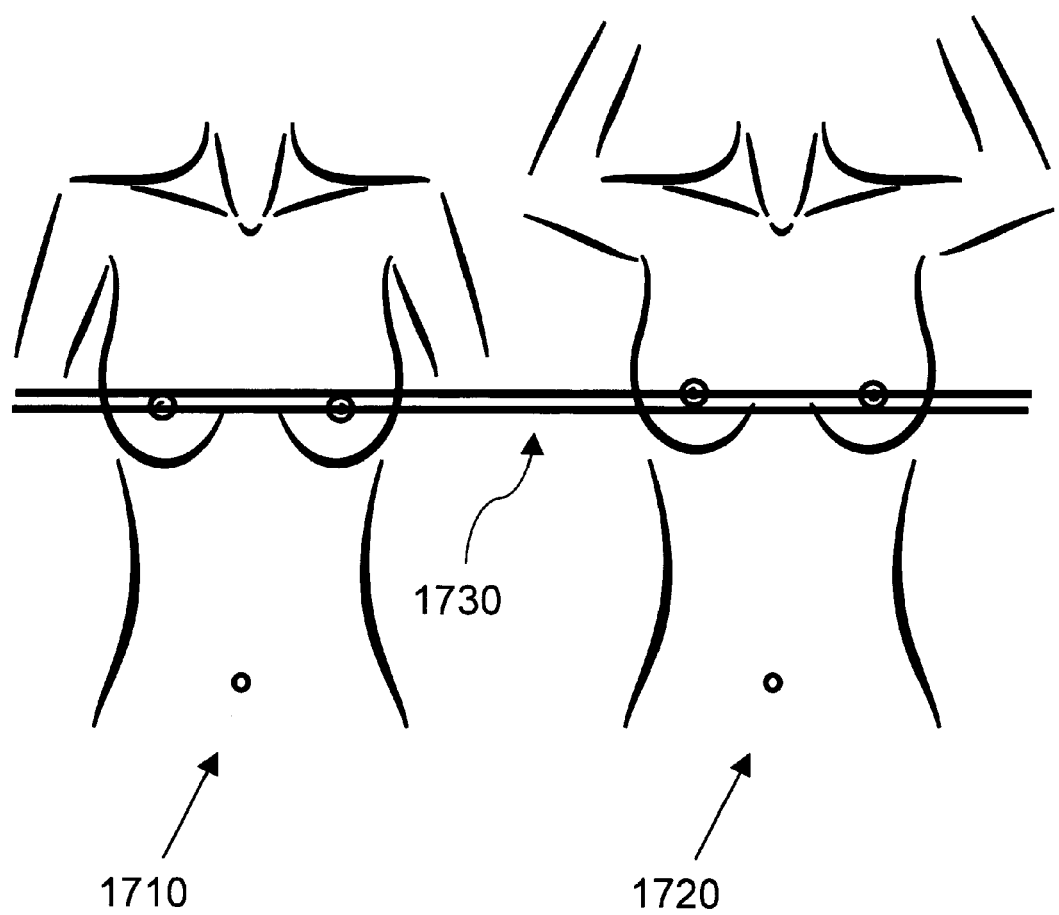
FIG. 17 shows according to an alternate embodiment of the present invention frontal views 1710, 1720 used to determine a resultant nipple position with displacement in interior to superior direction.

FIG. 17 shows an alternative method for determining the resultant inferior-to-superior displacement on the resultant breast shape by comparing the nipple positions of two 3-D representations. In the first 3-D representation 1710, the arms are in the proximity of the hips; the 3-D nipple features and position are identified relative to the same chest parameters (the first 3-D representation is also referred to as the 3-D representation herein). In the second 3-D representation 1720, the arms are elevated above the patient's head; the 3-D nipple features and position are identified relative to some chest parameters. The inferior to superior displacement of the nipple position is then determined by taking the position difference in corresponding nipple heights (i.e. determined by the difference in lines 1730).

As one of ordinary skill in the art will appreciate, various changes, substitutions, and alterations could be made or otherwise implemented without departing from the principles of the present invention. The methods describes could be programmed in executable computer code and stored on a computer medium or storage medium. The method steps could also be codes in various (independent) modules each including one or more method steps such as for example a measurement module, a feature recognition module, an asymmetry module, a breast volume module, an orientation module, a simulation module whereby one could further distinguish a breast shape simulation module or a nipple simulation module, or the like. The methods or parts of the steps as modules could also be integrated in semiconductor or computer chips capable of performing or executing the method steps, whereby the chips algorithms could be called and executed as part of an integrated system. The chips could for example be used in breast imaging or diagnostic devices or computer systems. In other words, the methods steps could be individual modules or means for executing the methods steps. Accordingly, the scope of the invention should be determined by the following claims and their legal equivalents.

What is claimed is:

1. A computer implemented method for assisting breast augmentation surgery planning, the method comprising:
   generating a three dimensional representation of an upper front torso of a woman;
   analyzing a rate of change of at least one contour present in the three dimensional representation of the upper front torso, wherein the analysis analyzes at least one anatomical feature of the upper front torso;
   constructing a virtual chest wall from the analysis wherein the virtual chest wall results in a realistic image of the upper front torso of the woman including an existing breast of the woman;
   generating from the virtual chest wall a three dimensional image of a resultant upper front torso including a resultant breast of the woman as it would appear after the breast augmentation surgery, thereby assisting breast augmentation surgery planning; and
   determining a volume value of the resultant breast wherein the volume value is equal to the sum of the implant volume plus the volume of the existing breast multiplied by a factor representing a degree of atrophy of the existing breast volume.

2. The method of claim 1, wherein the analyzing a rate of change step comprises automatically determining planes and orientations of the upper front torso of the woman including upper torso midline, coronal plane, sagittal plane, or traverse plane.

3. The method of claim 1, wherein the at least one anatomical feature includes one or both nipples, one or both areole, one or more axillary lines, axilla, one or more breast fold lines, sternum, sternal notch, or one or both clavicles.

4. The method of claim 1, further comprising determining a breast cup size of the resultant breast.

5. The method of claim 1, wherein the volume value is equal to the sum of the implant volume plus the volume of the existing breast multiplied by a factor ranging from 0.3 to 0.6.

6. The method of claim 1, further comprising analyzing an asymmetry of an anatomical feature present on the three-dimensional representation.

7. A computer-implemented method for assisting a woman in the planning of breast augmentation surgery, the method comprising the steps of:
   generating a three-dimensional representation of the upper front torso of the woman;
   performing a three-dimensional contour analysis by recognizing and analyzing the contours and the rate of change in the contours on the three-dimensional representation, wherein the three-dimensional contour analysis automatically recognizes and analyzes key anatomical features and locations of the upper front torso of the woman;
   constructing a virtual chest wall from the contoured three-dimensional representation by including a soft tissue envelope, wherein the constructed virtual chest wall results in a realistic image of the upper front torso of the woman including an existing breast; and
   generating, from the constructed virtual chest wall, a three dimensional image of a resultant upper front torso of the woman including a resultant breast, as it would appear after a breast augmentation surgery, thereby assisting the woman in the planning of the breast augmentation surgery; and
   determining a volume value of the resultant breast wherein the volume value is equal to the sum of the implant volume plus the volume of the existing breast multiplied by a factor representing a degree of atrophy of the existing breast volume.

8. The method of claim 7, wherein the three-dimensional contour analysis further automatically determines planes and orientations of the upper front torso of the woman including upper torso midline, coronal plane, sagittal plane, or traverse plane.

9. The method of claim 7, wherein recognition of key anatomical features and locations include one or both nipples, one or both areole, one or more axillary lines, axilla, one or more breast fold lines, sternum, sternal notch, or one or both clavicles.

10. The method of claim 7, wherein analysis of at least some of the key anatomical features and locations determines a plurality of breast-related direct point-to-point distances and a plurality of breast-related three-dimensional surface lines from the recognized key anatomical features.

11. The method of claim 7, wherein the plurality of breast-related direct point-to-point distances include breast base width distance, nipple to midsternal line distance, areola diameter, nipple to nipple distance, intermammary distance, breast fold line to nipple projection position distance, midclavicle to nipple distance, breast height distance, or any combination thereof.

12. The method of claim 7, further comprises determining a breast cup size of the resultant breast.

13. The method of claim 7, wherein the volume value is equal to the sum of the implant volume plus the volume of the existing breast multiplied by a factor ranging from 0.3 to 0.6.

14. A computer-implemented method for assisting a woman in the planning of breast augmentation surgery, the method comprising:
   generating a three-dimensional representation of the upper front torso of the woman;
   performing a three-dimensional contour analysis by recognizing and analyzing the contours and the rate of change in the contours on the three-dimensional representation, wherein the three-dimensional contour analysis automatically recognizes and analyzes key anatomical features and locations of the upper front torso of the woman;
   constructing a virtual chest wall from the contoured three-dimensional representation by including a soft tissue envelope, wherein the constructed virtual chest wall results in a realistic image of the upper front torso of the woman including an existing breast;

generating, from the constructed virtual chest wall, a three dimensional image of a resultant upper front torso of the woman, including a resultant breast, as it would appear after a breast augmentation surgery; and determining a cup size of the resultant breast, thereby assisting the woman in the planning of the breast augmentation surgery;

determining a volume value of the resultant breast wherein the volume value of the resultant breast is equal to the sum of the implant volume plus the volume of the existing breast multiplied by a factor representing a degree of atrophy of the existing breast volume.

15. The method of claim 14, wherein the volume value is equal to the sum of the implant volume plus the volume of the existing breast multiplied by a factor ranging from 0.3 to 0.6.

* * * * *

UNITED STATES PATENT AND TRADEMARK OFFICE
CERTIFICATE OF CORRECTION

PATENT NO. : 9,129,055 B2  Page 1 of 1
APPLICATION NO. : 14/137800
DATED : September 8, 2015
INVENTOR(S) : Mordaunt et al.

It is certified that error appears in the above-identified patent and that said Letters Patent is hereby corrected as shown below:

On the title page, item [56]

Page 2, column 2, line 22, delete "5(5):" and insert -- 54(5): --, therefor.

Page 2, column 2, line 24, delete "Suregery"," and insert -- Surgery", --, therefor.

In the specification

Column 1, line 14, delete "application" and insert -- applications --, therefor.

Column 3, line 28, delete "midstemal" and insert -- midsternal --, therefor.

Column 4, line 25, delete "fust" and insert -- first --, therefor.

Column 7, line 47, delete "midsternalline" and insert -- midsternal line --, therefor.

Column 10, line 32, delete "midstemal" and insert -- midsternal --, therefor.

Column 11, line 49, delete "midstemal" and insert -- midsternal --, therefor.

Column 11, line 51, delete "midstemal" and insert -- midsternal --, therefor.

Signed and Sealed this
Twenty-fourth Day of May, 2016

Michelle K. Lee
*Director of the United States Patent and Trademark Office*